United States Patent [19]

Koibuchi et al.

[11] Patent Number: 4,722,883

[45] Date of Patent: Feb. 2, 1988

[54] PROCESS FOR PRODUCING FINE PATTERNS

[75] Inventors: Shigeru Koibuchi; Asao Isobe, both of Hitachi; Daisuke Makino, Mito, all of Japan

[73] Assignee: Hitachi, Ltd., Japan

[21] Appl. No.: 894,122

[22] Filed: Aug. 7, 1986

Related U.S. Application Data

[63] Continuation of Ser. No. 608,165, May 8, 1984, abandoned.

[30] Foreign Application Priority Data

May 12, 1983 [JP] Japan ................................. 58-83176
Aug. 22, 1983 [JP] Japan ................................ 58-152959

[51] Int. Cl.$^4$ ........................... G03F 7/26; G03C 5/00
[52] U.S. Cl. .................................. 430/323; 430/197; 430/317; 430/325
[58] Field of Search ................ 430/326, 323, 197, 317

[56] References Cited

U.S. PATENT DOCUMENTS

| | | | |
|---|---|---|---|
| 2,848,328 | 8/1958 | Hepher | 430/197 |
| 3,595,656 | 7/1971 | Ruckert et al. | 430/197 |
| 3,869,292 | 3/1975 | Peters | 430/197 |
| 3,887,373 | 6/1975 | Hays et al. | 430/325 |
| 4,401,745 | 8/1983 | Nakane et al. | 430/197 |

*Primary Examiner*—Charles L. Bowers, Jr.
*Attorney, Agent, or Firm*—Antonelli, Terry & Wands

[57] ABSTRACT

Fine patterns with high degree of resolution and high resistance to etching can be produced by coating a solution of a photosensitive composition comprising (a) an aromatic azide compound and (b) an alkaline-aqueous-solution-soluble polymer on a substrate, exposing predetermined portions of the coated photosensitive composition to ultraviolet light, developing with an alkaline aqueous solution to form a resist pattern, and etching the substrate using said resist pattern as a mask.

8 Claims, 5 Drawing Figures

PROCESS FOR PRODUCING FINE PATTERNS

This is a continuation of U.S. patent application Ser. No. 608,165, filed May 8, 1984 abandoned.

BACKGROUND OF THE INVENTION

This invention relates to a process for producing fine patterns using a photosensitive composition excellent in developing properties for an alkaline aqueous solution and forming positive images. More in detail, this invention relates to a process for producing fine patterns using a photosensitive composition having high sensitivity to ultraviolet light, high resolving power and high resistance to etching.

With a rapid progress in the semiconductor industry in recent years, there has been required improvement in performance and properties in wide range for resist materials used for pattern formation. In order to meet such a requirement, there have been provided practically various kinds of photosensitive compositions, which have many advantages as well as disadvantages, respectively.

A typical fine pattern making technique having been employed in the field of semiconductor integrated circuits is ultraviolet lithography using a photoresist. The ultraviolet lithography is a very effective means for producing a large number of semiconductor integrated circuits in a short time.

As to resist materials used in the ultraviolet lithography, a typical negative type photoresist is a composition comprising a cyclized rubber and an aromatic azide compound. The cyclized rubber includes polybutadiene, polyisoprene, and the like and is used by adjusting the molecular weight, the degree of dispersion, and the like. The aromatic azide compound includes, for example, azidobenzal ketones such as 2,6-bis(4'-azidobenzal)-4-methylcyclohexanone, 2,6-bis(4'-azidobenzal)-cyclohexanone, etc. In the case of the negative type photoresist obtained by combining the cyclized rubber and the aromatic azide compound, a developing solution used at the time of development for dissolving uncured portions also swells cured portions of resist, which results in causing blisters and meandering in the resist. The swelling of the resist per se by the developing solution seems to be a main factor for lowering the degree of resolution. Therefore, it is impossible at present time to form fine patterns having a width of 0.5 μm to 0.2 μm with high precision by using the composition comprising a cyclized rubber and an aromatic azide compound.

On the other hand, a typical positive type photoresist is a photoresist composition comprising a novolac resin and a quinone diazide compound. The novolac resin includes a phenol novolac resin, a cresol novolac resin, etc. The quinone diazide compound used as photosensitizer includes o-naphthoquinonediazide, etc. Positive type photoresists are generally good in the degree of resolution. This is because the base resin is an organic material such as a novolac resin and the developing solution is an alkaline aqueous solution, so that the resin portion is not swelled at the time of development and only the portion exposed to ultraviolet light is dissolved.

As to etching of a substrate using a resist as mask, there are wet etching and dry etching. Wet etching has been used widely but there is a limitation thereto considering precision of fine patterns and easy peeling of resist at the time of side etching or wet etching.

Considering the above-mentioned points with regards to photoresist materials, cyclized rubber series negative type photoresists are good in resistance to dry etching, but since they are low in the degree of resolution as mentioned above, it is difficult to use them for producing fine patterns.

On the other hand, phenol resin series positive type photoresists are good in the degree of resolution and resistance to etching and are characterized by the positive type.

As to the light source, Japanese Patent Appln Kokai (Laid-Open) No. 162744/81 discloses the use of far ultraviolet light, which requires special apparatus and cannot be used generally.

Further, Japanese Patent Appln Kokoku (Post-Exam Publn) Nos. 22082/70 and 34902/78 disclose that a mixture of a novolac resin or the like and an azide compound is useful as photosensitive resin composition. But these references are quite silent on resistance to etching of such a photosensitive resin composition.

SUMMARY OF THE INVENTION

It is an object of this invention to overcome the defects of known photoresists mentioned above and to provide a process for producing fine patterns using a photosensitive composition excellent in fine processing, being able to be used as a negative type resist and also good in resistance to etching.

This invention provides a process for producing a fine pattern which comprises (1) a step of coating on a substrate a photosensitive composition comprising (a) a compound of the formula:

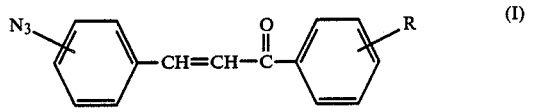

wherein R is an alkyl group, an alkoxy group, a hydroxyl group, a hydroxyalkyl group or an aminoalkyl group, and R has 10 or less carbon atoms, and (b) an alkaline-aqueous-solution-soluble polymer which can be insolubilized in an alkaline aqueous solution by photochemical curing with the component (a), (2) a step of exposing predetermined portions of the coated photosensitive composition to ultraviolet light to lower the solubility of the exposed portions in an alkaline aqueous solution, (3) a step of developing the thus treated coated photosensitive composition with an alkaline aqueous solution to form a resist pattern by removing portions not exposed to ultraviolet light, and (4) a step of etching using said resist pattern as a mask to form a fine pattern on the substrate.

DESCRIPTION OF THE PREFERRED EMBODIMENTS

Figure 1:
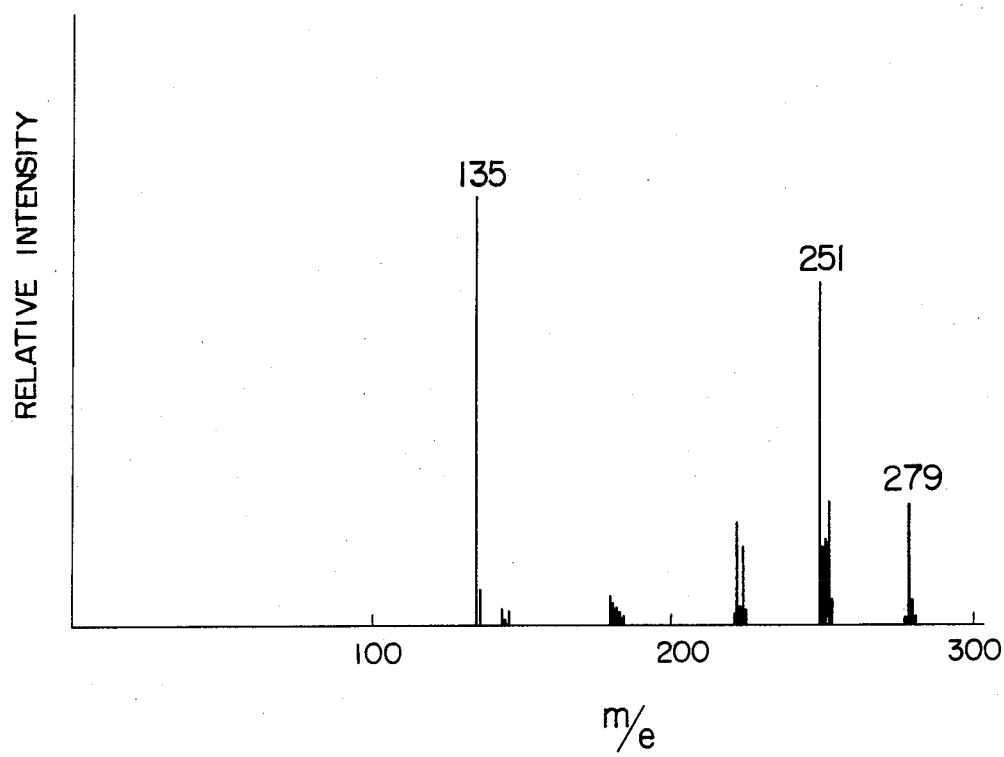
FIG. 1 shows molecular ion peaks in a mass spectrum of 4-azido-2'-methoxychalcone, which is a novel compound, used as azide compound in this invention.

The aromatic azide compound (a) in the photosensitive composition used in the process for forming patterns of this invention is represented by the formula:

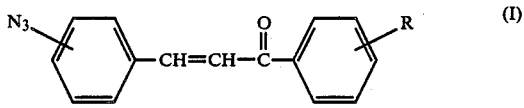 (I)

wherein R is an alkyl group having 10 or less carbon atoms, preferably having 5 or less carbon atoms such as —$CH_3$, —$C_2H_5$, etc., an alkoxy group having 10 or less carbon atoms, preferably having 5 or less carbon atoms such as —$OCH_3$, —$OC_2H_5$, etc., a hydroxyalkyl group having 10 or less carbon atoms, preferably having 5 or less carbon atoms such as —$CH_2CH_2OH$, etc, an aminoalkyl group having 10 or less carbon atoms, preferably having 5 or less carbon atoms such as

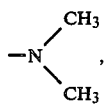

etc, or a hydroxyl group.

Preferable examples of the aromatic azide compound of the formula (I) are 4'-azidobenzal-4-methylacetophenone, 3'-azidobenzal-4-hydroxyacetophenone, 4'-azidobenzal-3-ethoxyacetophenone, 4'-azidebenzal-4-ethylolacetophenone, 3'-azidobenzal-4-(N,N-dimethylamino)ethylacetophenone, 4-azido-2'-methoxychalcone, 4'-azidobenzal-3-methoxyacetophenone, 4'-azidobenzal-4-methoxyacetophenone, etc.

These aromatic azide compounds can be prepared, for example, by alkali condensation reaction of azidobenzaldehyde with an acetophenone compound.

Among the aromatic azide compounds mentioned above, 4-azido-2'-methoxychalcone of the formula:

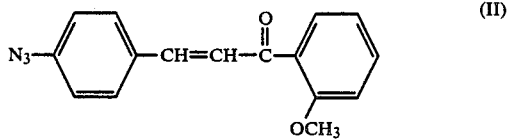 (II)

is a novel compound. This compound can be prepared by reacting p-azidobenzaldehyde with 2-methoxyacetoplenone using an alkaline compound as catalyst. It is preferable to react p-azidobenzaldehyde with 2-methoxyacetophenone in almost equimolar amounts.

Examples of the alkaline compound used as catalyst are hydroxide of alkali metals such as sodium hydroxide, potassium hydroxide, etc.

The above-mentioned reactions are carried out in a solvent which can dissolve the alkaline compound. Examples of the solvent are water and alcohols such as methanol and ethanol.

The reaction temperature is not particularly limited but is preferably 0° to 40° C. from the viewpoint of stability of the reaction product and reaction rate.

Since the compound of the formula (I) is photosensitive, it is preferable to carry out the reaction in a yellow light.

As the component (b) used in the photosensitive composition, there is used an alkaline-aqueous-solution-soluble polymer which can be insolubilized in an alkaline aqueous solution by photochemical curing with the component (a).

The alkaline-aqueous-solution-soluble polymer means a high polymer having hydroxyl groups and/or carboxyl groups. Examples of such a polymer are novolac resins (condensates of formaldehyde with phenol, cresol, or other alkylphenol), polyhydroxystyrene resins, acrylic or methacrylic polymers, etc. These polymers include homocondensates, co-condensates, homopolymers and copolymers. Further, these polymers can be used alone or as a mixture thereof.

These resins are also available commercially. For example, the novolac resins include a phenol novolac resin, a cresol novolac resin, a phenol-cresol novolac resin, etc; the polyhydroxystyrene resins include poly(p-vinylphenol) and a brominated poly(p-vinylphenol), etc.; and the acrylic or methacrylic polymers include a homopolymer of acrylic acid or methacrylic acid, copolymers of acrylic acid or methacrylic acid with an acrylic ester or methacrylic ester, and copolymers of acrylic acid or methacrylic acid with styrene.

The alkaline-aqueous-solution-soluble polymer should be capable of forming a film after removal of the solvent and therefore should have a number average molecular weight of preferably at least 500, and more preferably 1000 or more in consideration of heat resistance of the resulting photosensitive composition.

The photosensitive composition used in this invention is intended to react in the ultraviolet region considering the components included therein. That is, the compound represented by the formula (I) has a structure wherein the benzene rings and the moiety of

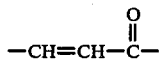

resonate, so that it has the maximum absorption wavelength (λmax) at near 300 nm to 500 nm. For example, 4'-azidobenzal-4-methylacetophenone has λmax at 330 nm, 3'-azidobenzal-4-hydroxyacetophenone λmax at 330 nm, 4'-azidobenzal-3-ethoxyacetophenone λmax at 340 nm, 3'-azidobenzal-4-(N,N-dimethylamino)ethylacetophenone λmax at 390 nm, etc.

Resistance to etching, particularly resistance to dry etching can be improved by selecting a proper base resin (the component (b)). That is, the base resin having aromatic rings such as novolac resins and polyhydroxystyrene resins can improve resistance to dry etching remarkably.

Further, when 4-azido-2'-methoxychalcone is used as the component (a), the resulting photosensitive composition is improved remarkably in storage stability when dissolved in an organic solvent and the change of viscosity of such a solution with the lapse of time is very small.

The photosensitive composition is dissolved in a proper organic solvent to give a varnish and coated on a substrate.

The organic solvent should dissolve both the components (a) and (b) of the photosensitve composition. Examples of the organic solvent are ketones such as acetone, methyl ethyl ketone, methyl isobutyl ketone, cyclohexanone, etc.; Cellosolves such as methyl Cellosolve, ethyl Cellosolve, methyl Cellosolve acetate, ethyl Cellosolve acetate, etc.; esters such as ethyl acetate, butyl acetate, isoamyl acetate, etc. These solvents can be used alone or as a mixture thereof.

The organic solvent is preferably used in an amount of 100 to 10000 parts by weight per 100 parts by weight of the total of the compound of the formula (I) (the component (a)) and the resin component (b).

The weight ratio of the components (a) to (b) ((a)/(b)) in the composition is preferably 0.05/1 to 1/1, more preferably 0.05/1 to 0.5/1.

The photosensitive composition may further contain conventional additives in addition to the base resin (b) and the aromatic azide of the formula (I) (a). Examples of such additives are a thermal polymerization inhibitor for the purpose of securing storage stability, a halation inhibitor for the purpose of preventing halation due to the light reflection from the substrate, an adhesion improver for the purpose of improving the adhesion to the substrate, dyes, pigments, fillers, fire retardants, photosensitizers, etc.

The steps for producing fine patterns are explained in detail below.

As the coating method of the photosensitive composition on the supporting substrate in the step (1), there can be employed a spin coating method using a spinner, a dipping method, a spraying method, a printing method, and the like depending on the purposes.

As the substrate, there can be used a silicon wafer, a ceramic substrate, a substrate deposited with aluminum or chromium, etc.

The coated photosensitive composition is then dried at a proper temperature such as 120° C. or lower, preferably 70° to 100° C., to give a dried film. The thickness of the coating film can be adjusted by the coating means, the solid content of the varnish, and the viscosity of the varnish.

In the step (2), predetermined portions of the photosensitive composition coated on the substrate are exposed to ultraviolet light to lower the solubility of the portions exposed to ultraviolet light in an alkaline aqueous solution which is a developing solution.

Most suitable irradiating amount necessary for photochemical curing is in the range of 0.5 to 5000 mJ/cm$^2$, preferably 1 to 1000 mJ/cm$^2$ in the case of ultraviolet light. The irradiating amount can be changed depending on the purposes.

As to a method for exposing to ultraviolet light, there can be employed either a direct contacting method or a projecting method to produce patterns.

In the step (3), a resist pattern is formed by removing the portions not exposed to ultraviolet light in the step (2) with a developing solution, that is, an alkaline aqueous solution. Examples of the alkaline aqueous solution are an aqueous solution of tetraalkylammonium hydroxide such as tetramethylammonium hydroxide, an aqueous solution of inorganic compound such as potassium hydroxide, tribasic sodium phosphate, sodium hydroxide, or the like. These alkaline aqueous solutions are used usually in a concentration of 5% by weight or less.

The development can be carried out by a conventional method such as a dipping method, a spray method, and the like. Preferable temperature for the development is in the range of 5° to 60° C. The rate of development depends on the temperature conditions, so that a proper one can be selected depending on the purposes.

After the development, the developing solution is removed from the substrate by rinsing to clean the surface of substrate. As the rinsing solution, the use of water is preferable.

In the step (4), etching is conducted using the resist pattern as a mask to produce a fine pattern on the surface of the substrate.

As the etching method, both the wet etching and dry etching can be employed. In the case of forming a fine pattern having a line width of 3 μm or less, dry etching is preferable.

In the case of dry etching, there can be used such a gas as $CF_4$, $C_2F_8$, $C_4F_8$, $CCl_4$, $BCl_3$, $Cl_2$, $HCl$, $H_2$, etc., for etching. These gases can be used alone or as a mixture thereof depending on the kind of substrate to be treated. The gas pressure, etching temperature, and etching time can be selected properly depending on the degree of processing of substrate. Usually employed gas pressure is 100 Torr or less, and usually employed etching temperature is 10° to 100° C.

As the wet etching agent, there can be employed an aqueous solution of hydrofluoric acid, ammonium fluoride, or the like in the case of a silicon oxide film; an aqueous solution of phosphoric acid, acetic acid, nitric acid, or the like in the case of aluminum; and an aqueous solution of ammonium cerium (IV) nitrate, etc.

Etching conditions can be determined depending on the combination of the kind of substrate on which a fine pattern is to be produced and the photosensitive composition, the concentration of the wet etching agent in a reactor, the reaction temperature, the reaction time, and the like. There are no special limitations thereto and any conventional ones can be used.

After the etching, the portions exposed to ultraviolet light and still remaining on the substrate are removed by using a release agent such as J-100 (manufactured by Nagase Chemical Co., Ltd.) or oxygen plasma.

Other steps than the above-mentioned steps (1) to (4) may be added depending on the purposes, if necessary. For example, there are a step of rinsing for the purpose of washing and removing the developing solution from the substrate after the development step (3) (usually by using water), a step of pre-treatment before the coating step (1) for the purpose of improving adhesiveness of the photosensitive composition to the substrate on which a fine pattern is to be formed, a step of baking before or after the development step (3), a step of irradiation with ultraviolet light before the etching step (4).

This invention is illustrated by way of the following Examples, in which all the parts and percents are by weight unless otherwise specified.

EXAMPLE 1

A solution of a photosensitive composition was prepared by dissolving 10 parts of phenol novolac resin in 90 parts of cyclohexanone, followed by dissolution of 1.5 parts of 4'-azidobenzal-3-ethoxyacetophenone. The solution was filtered under pressure by using a filter having openings of 1 μm.

The resulting solution was spin coated on a silicon wafer by using a spinner and dried at 90° C. for 20 minutes to give a coating film having a thickness of 0.8 μm. This coating film was directly covered with a photomask having a striped pattern made of quartz and irradiated with ultraviolet light from a mercury lamp of 250 W at a distance of 30 cm for 5 seconds. Then development was conducted by spraying a 0.15 N aqueous solution of potassium hydroxide, followed by washing with water to give a relief pattern with sharp end surfaces. In this Example, a pattern having separated lines and spaces with the minimum width of 1 μm could be transferred.

Then, a reactive sputter etching (2.3 A, 20 Pa) was conducted for 20 minutes using a mixture of gases of $C_4F_8$ and He (1:1 by volume). The weight loss of the resist was 30%.

This value is superior in resistance to dry etching to the value of 35% of AZ-1350J (a trade name available from Shipley Corp.) which is the best in resistance to dry etching among known photoresists, under the same conditions. This means that a dry etching process can be applied to the substrate using said resist as mask.

EXAMPLE 2

A solution of a photosensitive composition was prepared by dissolving 10 parts of cresol novolac resin in 120 parts of ethyl Cellosolve acetate, followed by dissolution of 2 parts of 4'-azidobenzal-2-ethoxyacetophenone. The solution was filtered under pressure by using a filter having openings of 1 μm.

The resulting solution was spin coated on a ceramic substrate by using a spinner and dried at 80° C. for 20 minutes to give a coating film having a thickness of 0.8 μm. The coating film was directly covered with a photomask having a striped pattern made of quartz and irradiated with ultraviolet light for 5 seconds by using the same mercury lamp as used in Example 1. Then, development was conducted by spraying a 0.2 N aqueous solution of sodium hydroxide, followed by washing with water to give a relief pattern with sharp end surfaces.

The resistance to dry etching was measured in the same manner as described in Example 1. The weight loss was 28%.

EXAMPLE 3

A solution of a photosensitive composition was prepared by dissolving 10 parts of poly(p-vinylphenol) and 3 parts of 4'-azidobenzal-4-hydroxyacetophenone in 120 parts of ethyl Cellosolve acetate. The solution was filtered under pressure by using a filter having openings of 0.2 μm.

The resulting solution was spin coated on a ceramic substrate by using a spinner and dried at 70° C. for 20 minutes to give a coating film having a thickness of 10 μm. The coating film was irradiated with ultraviolet light for 5 seconds in the same manner as described in Example 1. Then, development was conducted by spraying a 0.1 N aqueous solution of tetramethylammonium hydroxide, followed by washing with water to give a relief pattern with sharp end surfaces. In this Example a pattern having repeated lines and spaces with the minimum width of 1.5 μm could be produced. The resistance to dry etching was the same as in Example 1.

EXAMPLE 4

A solution of a photosensitive composition was prepared by dissolving 10 parts of phenol novolac resin, 3 parts of 3'-azidobenzal-4-ethoxyacetophenone in 90 parts of cyclohexanone. The solution was filtered under pressure by using a filter having openings of 0.2 μm.

The resulting solution was spin coated on a silicon wafer by using a spinner and dried at 70° C. for 20 minutes to give a coating film having a thickness of 0.8 μm. The coating film was irradiated with ultraviolet light for 5 seconds in the same manner as described in Example 1. Then, development was conducted by spraying a 0.09 N aqueous solution of tetramethylammonium hydroxide, followed by washing with water to give a relief pattern with sharp end surfaces. In this Example, a pattern having repeated lines and spaces with the minimum width of 1.0 μm could be produced. The resistance to dry etching was the same as in Example 1.

EXAMPLE 5

(1) [Synthesis of 4-azido-2'-methoxychalcone]

In a 500-ml flask were placed 15 g of 2-methoxyacetophenone (made by Aldrich Co., 99% purity), 15 g of p-azidobenzaldehyde (manufactured by Kanto Chemical Co., Ltd.), 50 g of 10% aqueous solution of NaOH, and 50 g of methanol. The mixture was stirred in a yellow light at 25° C. for 24 hours. After completion of the reaction, the deposited crystals were filtered, washed with water, dried, and recrystallized from ethanol.

The 2-methoxyacetophenone used had a purity of 99% and contained almost no isomers different in the position of methoxy substituent. It is sure that the position of methoxy substituent in 2-methoxyacetophenone does not vary during the synthesis in the aqueous alkaline solution.

The thus obtained 4'-azidobenzal-2-methoxyacetophenone was identified by the following analyses:

(A) Mass spectrometry (200° C., 50 eV), m/e=279

FIG. 1 shows an example of the spectrum.

(B) IR spectrometry (KBr method)

Figure 2:
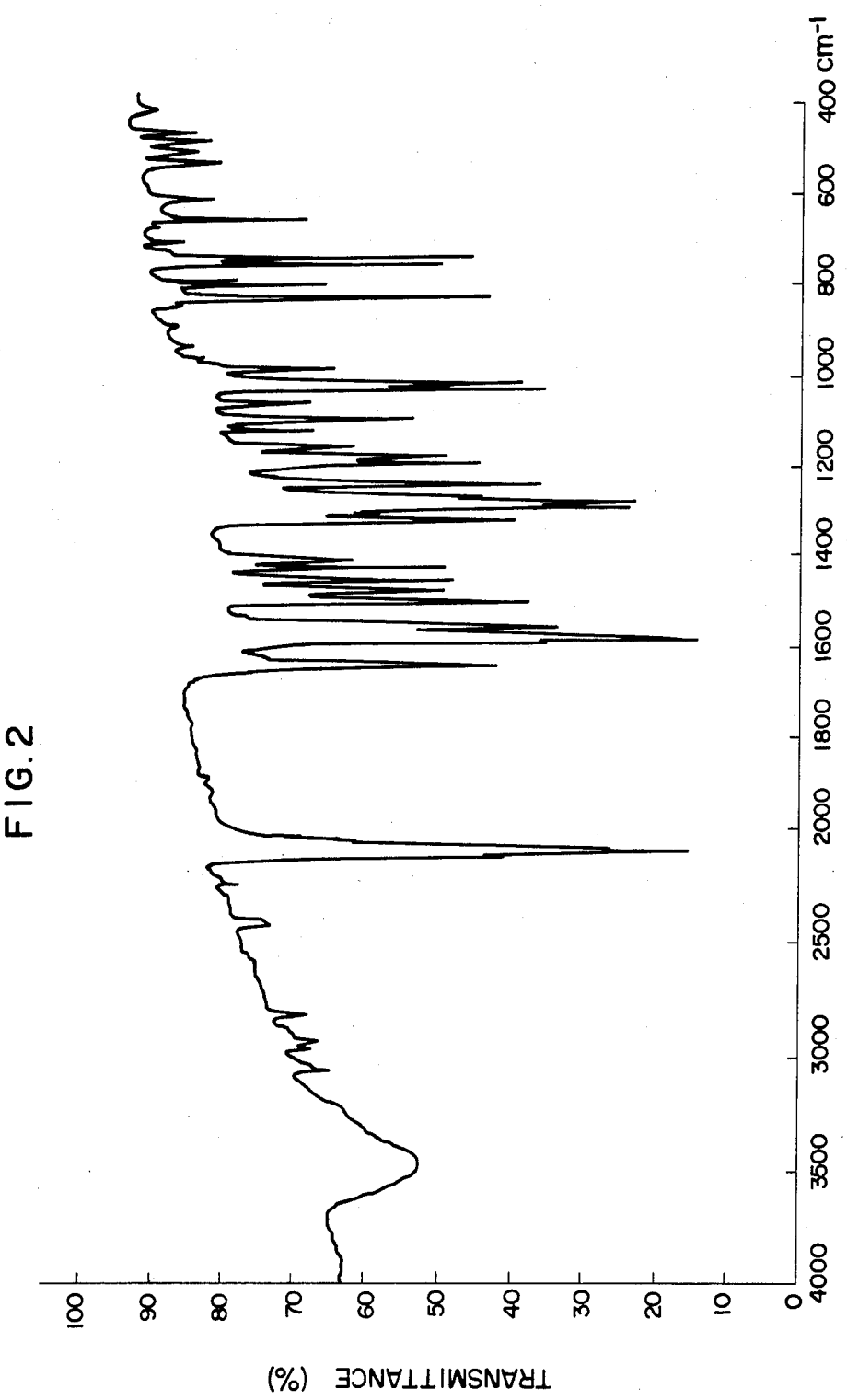
FIGS. 2 and 3 are infrared absorption and NMR spectra, respectively, of the above-mentioned azide compound.

FIG. 2 shows an example of the spectrum. A strong absorption due to the azido group ($-N_3$) was observed at 2100 cm$^{-1}$.

(C) NMR spectrometry ($^1$H-NMR)

Figure 3:
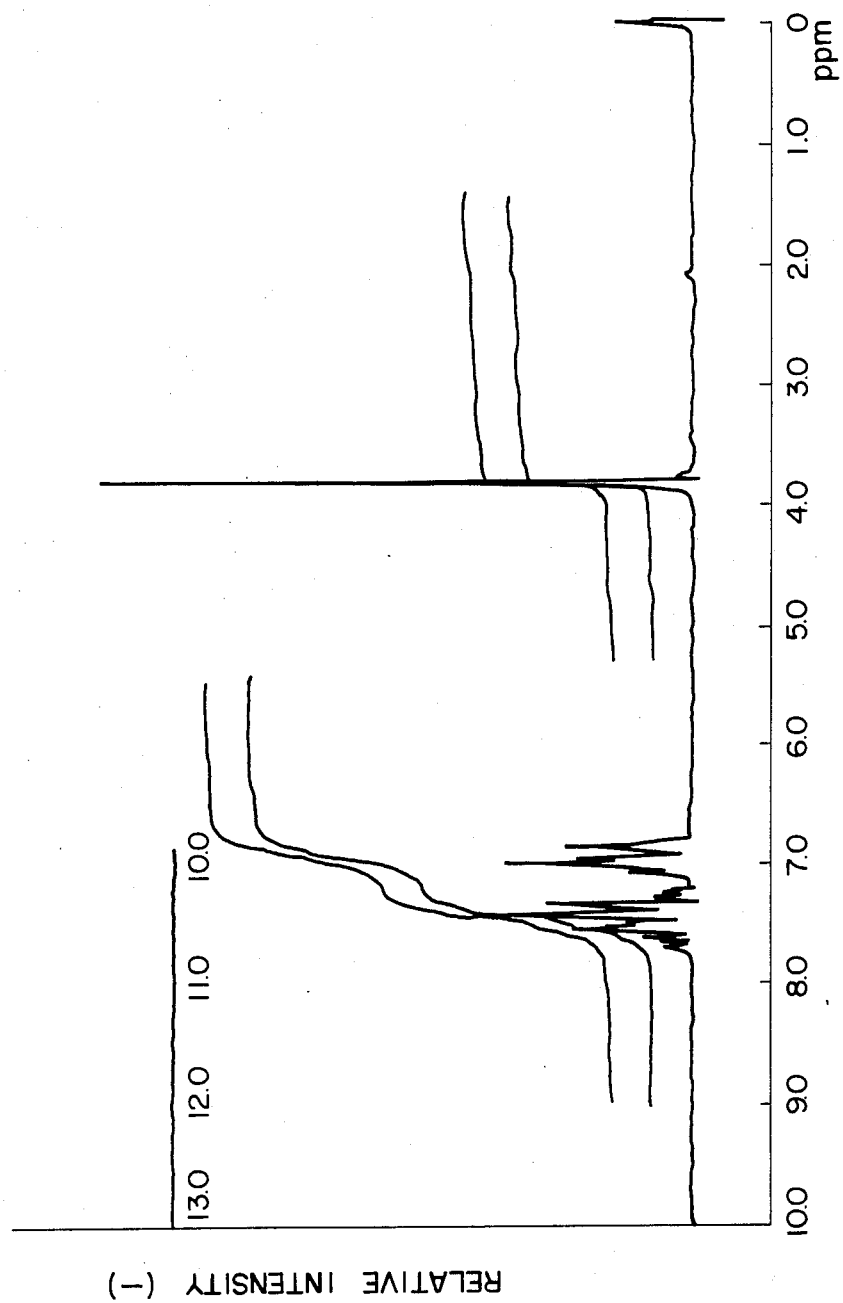

FIG. 3 shows an example of the spectrum. In addition, spectra of the 3-methoxy and 4-methoxy isomers are shown in FIGS. 4 and 5, respectively.

From FIG. 3, $-OCH_3$ and

Figure 4:
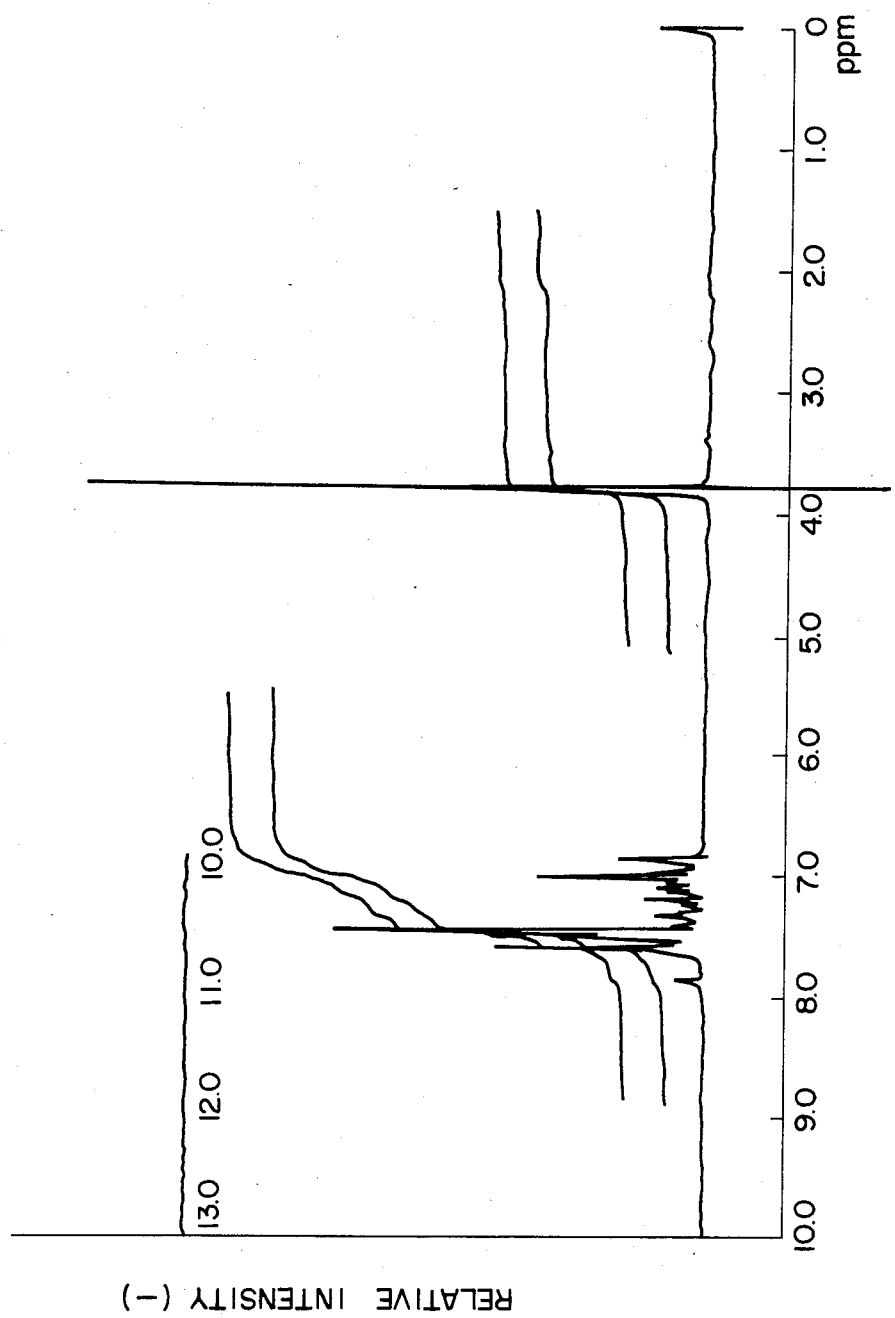
FIGS. 4 and 5 are respective NMR spectra of two compounds analogous to the above-mentioned azide compound.
Figure 5:
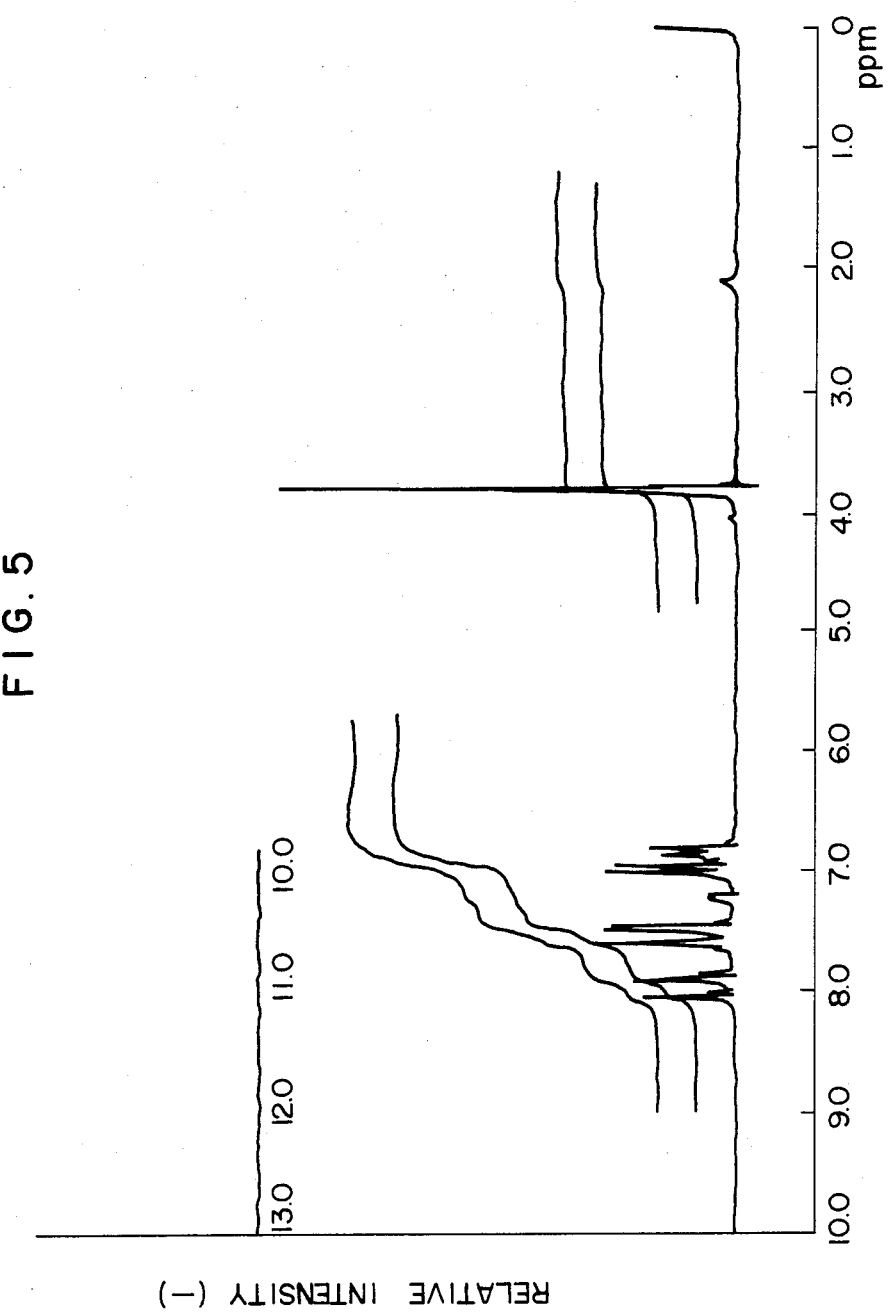

were identified: that is, the presence of 2-methoxy group was confirmed by comparing FIG. 3 with FIGS. 4 and 5, which show comparative examples. The spectrum between 6.8 ppm and 8.1 ppm differs depending upon the position of methoxy substituent.

(D) Crystal color: Yellow (E) Maximum absorption in ultraviolet absorption spectrum: 330 nm (in ethanol)

(F) Melting point: 90° C.

(2) [Production of fine pattern]

A photosensitive composition was prepared by dissolving 1 part of 4-azido-2'-methoxychalcone synthesized above and 5 parts of poly(p-vinylphenol) (manufactured by Maruzen Oil Co., Ltd.) in 25 parts of cyclohexanone. The composition was spin coated at 3000 rpm on a silicon wafer for 30 seconds, and was dried to form a photosensitive coating about 1 μm thick.

The thus coated substrate was exposed to ultraviolet light at an intensity of 10 mW/cm² (measured on the ray of 365 nm in wavelength) for 3 seconds through a chrome mask by using a 250 W mercury lamp. Then, unexposed portions were developed by using a 1% aqueous solution of tetramethylammonium hydroxide to produce a resist pattern having repeated lines and spaces with 1.5 μm wide. Then dry etching was conducted by using CF₄ gas and barrel type dry etching apparatus (RFG-500A manufactured by Yamato Kagaku K.K., Japan) with a power of 100 W and a pressure of 0.4 Torr. Thus the silicon oxide film was etched by using said resist pattern as a mask.

Then, the resist pattern was pealed off using oxygen gas in the dry etching apparatus mentioned above with a power of 100 W and a pressure of 1 Torr for 20 minutes to form an oxide film having a pattern of repeated lines and spaces with 1.5 μm wide, respectively.

EXAMPLE 6

A photosensitive composition was prepared by dissolving 1 part of 4-azido-2'-methoxychalcone prepared in Example 5 and 4 parts of a cresol novolac resin (PSF-2807 a tradename manufactured by Gun-ei Kagaku K.K.) in 25 parts of ethyl Cellosolve acetate. The composition was spin coated on a silicon wafer at 3000 rpm for 30 seconds and was dried to form a photosensitive coating about 1 μm thick.

The photosensitive coating was exposed to ultraviolet light through a chrome mask for 4 seconds by using the same mercury lamp as used in Example 5. Then the coating was treated with a 2% aqueous tetramethylammonium hydroxide solution to dissolve and remove the unexposed portions of the coating, thus forming a pattern of parallel lines with each 2 μm wide and 2 μm of spacing.

An etching agent was prepared by mixing 85% phosphoric acid, 100% acetic acid and 70% nitric acid in a weight ratio of 85:13:3 in a beaker. Then, the silicon wafer having the resist pattern formed thereon was placed in the beaker for 10 minutes to etch an aluminum film. After etching, the thus treated silicon wafer was taken out and the resist pattern was peeled off by using the oxygen plasma in the same manner as described in Example 5 to form the aluminum film having a pattern of repeated lines and spaces with 2 μm wide, respectively.

EXAMPLE 7

A photosensitive composition was prepared by dissolving 1 part of 4-azido-2'-methoxychalcone synthesized in Example 5 and 4 parts of a 4:6 (molar ratio) methacrylic acid-styrene copolymer in 40 parts of methyl Cellosolve acetate.

The composition was spin coated on a silicon wafer in the same manner as described in Example 5 to form a photosensitive coating about 1 μm thick.

The photosensitive coating was exposed to ultraviolet light through a chrome mask for 5 seconds by using the same mercury lamp as used in Example 5. Then the coating was treated with a 2% aqueous tetramethylammonium hydroxide solution to dissolve and remove the unexposed portions of the coating, thus forming a pattern of parallel lines with each 1.5 μm wide and 1.5 μm of spacing.

Dry etching and peeling of the resist pattern were conducted in the same manner as described in Example 5 to give an oxide film having a pattern of repeated lines and spaces with 1.5 μm wide, respectively.

As mentioned above, according to the process of this invention, fine patterns with high degree of resolution and high resistance to etching can be produced with remarkably high precision by using ultraviolet light and a negative type material.

What is claimed is:

1. A process for producing a fine pattern which comprises
   (1) a step of coating on a substrate a solution of a photosensitive composition comprising an admixture of
      (a) 4-azido-2'-methoxychalcone,
      (b) an alkaline-aqueous-solution-soluble polymer which can be insolubilized in an alkaline aqueous solution by photochemical curing with the component (a), the weight ratio of component (a) to (b) in the admixture being at least 0.05/1,
      (c) an organic solvent in which the 4-azido-2'-methoxychalcone has excellent solubility, said solution exhibiting little viscosity change with a lapse of time when stored, and said solvent being selected from the group consisting of a ketone, a cellusolve and an ester or a mixture thereof, the content of the solvent in the composition being 100 to 10,000 parts by weight per 100 parts by weight of the total of component (a) and (b).
   (2) a step of drying said coating,
   (3) a step of exposing predetermined portions of the coated photosensitive composition to ultraviolet light to lower the solubility of the exposed portions in an alkaline aqueous solution,
   (4) a step of developing the thus treated coating photosensitive composition with an alkaline aqueous solution to form a resist pattern by removing portions not exposed to ultraviolet light, and
   (5) a step of etching portions of the substrate exposed by the development and not covered with the resist pattern to form a fine pattern on the substrate.

2. A process according to claim 1, wherein the weight ratio of the component (a) to the component (b) in the admixture composition is 0.05/1 to 1/1.

3. A process according to claim 1, wherein the component (b) in the photosensitive composition is a homo-condensated novolac resin, a co-condensated novolac resin, a polyhydroxystyrene homopolymer, a polyhydroxystyrene copolymer, and acrylic or methlacrylic homopolymer or an acrylic or methacrylic copolymer.

4. A process according to claim 1, wherein the alkaline aqueous solution for development is an aqueous solution of an inorganic compound or tetraalkylammonium hydroxide.

5. A process according to claim 1, wherein the etching is dry etching.

6. A process according to claim 1, wherein the etching is wet etching.

7. A process to claim 1, wherein the solvent is selected from the group consisting of acetone, methyl ethyl ketone, methyl isobutyl ketone, cyclohexanaoanae, methyl Cellosolve, ethyl Cellosolve, methyl Cellosolve acetate, ethyl Cellosolve acetate, ethyl acetate, butyl acetate and isoamyl acetate.

8. A process according to claim 1 further comprising the step of storing the solution of the photosensitive composition

* * * * *